(12) United States Patent
Gliner et al.

(10) Patent No.: US 10,188,465 B2
(45) Date of Patent: Jan. 29, 2019

(54) AUTOMATIC ENT SURGERY PREPLANNING USING A BACKTRACKING MAZE PROBLEM SOLUTION

(71) Applicant: Biosense Webster (Israel) Ltd., Yokneam (IL)

(72) Inventors: Vadim Gliner, Haifa (IL); Fady Massarwi, Baka Al Gharbiyya (IL); Akram Zoabi, Kfar Masser (IL); Itamar Bustan, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 63 days.

(21) Appl. No.: 15/222,240

(22) Filed: Jul. 28, 2016

(65) Prior Publication Data

US 2017/0056112 A1 Mar. 2, 2017

Related U.S. Application Data

(60) Provisional application No. 62/209,946, filed on Aug. 26, 2015.

(51) Int. Cl.
*G06T 7/00* (2017.01)
*A61B 34/10* (2016.01)
(Continued)

(52) U.S. Cl.
CPC .............. *A61B 34/10* (2016.02); *A61B 5/055* (2013.01); *A61B 6/032* (2013.01); *A61B 6/501* (2013.01);
(Continued)

(58) Field of Classification Search
CPC ....... A61B 6/032; A61B 6/501; A61B 6/5247; A61B 34/10; A61B 5/055; G06T 7/0012
See application file for complete search history.

(56) References Cited

U.S. PATENT DOCUMENTS 7,720,521 B2 5/2010 Chang et al.
8,116,847 B2 2/2012 Gattani et al.
(Continued)

FOREIGN PATENT DOCUMENTS

WO WO 2010/076673 A1 7/2010
WO WO 2014/139024 A1 9/2014

OTHER PUBLICATIONS

Swennen, Gwen R.J., Molleman, Wouter, Schutyser, Filip ("Three-Dimensional Treatment Planning of Orthognathic Surgery in the Era of Virtual Imaging")2009 American Association of Oral and Maxillofacial Surgeons.*

(Continued)

*Primary Examiner* — Kim Y Vu
*Assistant Examiner* — Molly Delaney
(74) *Attorney, Agent, or Firm* — Frost Brown Todd LLC

(57) ABSTRACT

A method, consisting of receiving a computerized tomography scan of at least a part of a body of a patient, and identifying voxels of the scan that correspond to regions in the body that are traversable by a probe inserted therein. The method also includes displaying the scan on a screen and marking thereon selected start and termination points for the probe. A processor finds a path from the start point to the termination point consisting of a connected set of the identified voxels. The processor also uses the scan to generate a representation of an external surface of the body and displays the representation on the screen. The processor then renders an area of the external surface surrounding the path locally transparent in the displayed representation, so as to make visible on the screen an internal structure of the body in a vicinity of the path.

20 Claims, 7 Drawing Sheets

(51) Int. Cl.
*A61B 6/03* (2006.01)
*A61B 6/00* (2006.01)
*A61B 5/055* (2006.01)
*G06T 15/08* (2011.01)

(52) U.S. Cl.
CPC .......... *A61B 6/5247* (2013.01); *G06T 7/0012* (2013.01); *G06T 15/08* (2013.01); *A61B 2034/105* (2016.02); *A61B 2034/107* (2016.02); *G06T 2207/10081* (2013.01); *G06T 2207/10088* (2013.01); *G06T 2207/20101* (2013.01); *G06T 2207/30004* (2013.01)

(56) References Cited

U.S. PATENT DOCUMENTS

| | | |
|---|---|---|
| 8,160,676 B2 | 4/2012 | Gielen et al. |
| 9,037,215 B2 | 5/2015 | Higgins et al. |
| 2013/0328869 A1* | 12/2013 | Choi ...................... G06T 19/20 345/419 |
| 2014/0330115 A1* | 11/2014 | Schildkraut .......... A61B 6/5217 600/425 |
| 2016/0007842 A1 | 1/2016 | Govari et al. |
| 2017/0000564 A1* | 1/2017 | Gordon .............. A61B 17/1739 |

OTHER PUBLICATIONS

Beyer, Johanna, Hadwiger, Markus, Wolfsberger, Stefan, Buhler, Kajita "High-Quality Multimodal Volume Rendering for Preoperative Planning of Neurosurgical Interventions" IEEE Transactions on Visualization and Computer Graphics, vol. 13, No. 6, 2007.*
European Search Report and Written Opinion dated Feb. 2, 2017 for Application No. EP 16185774.3, 5 pgs.
U.S. Appl. No. 62/209,946, filed Aug. 26, 2015.

* cited by examiner

AUTOMATIC ENT SURGERY PREPLANNING USING A BACKTRACKING MAZE PROBLEM SOLUTION

CROSS-REFERENCE TO RELATED APPLICATION

This application claims the benefit of U.S. Provisional Patent Application 62/209,946, filed Aug. 26, 2015, which is incorporated herein by reference.

FIELD OF THE INVENTION

This invention relates generally to surgery, and specifically to preplanning of invasive nasal sinus surgery.

BACKGROUND OF THE INVENTION

The paranasal sinuses comprise four separate pairs of three-dimensional (3D) air-filled spaces which are in proximity to the nasal cavity. Invasive surgery of a selected region of the sinuses may be considered necessary, for example, in the case of severe sinusitis, using a catheter to reach the region. Typically, at present, prior to performing such invasive surgery, a computerized tomography (CT) scan of a selected region of one of the sinuses and its environs is taken. A physician analyzes the scan in order to select the best path, typically the shortest path, from a nostril to the selected region to be taken by the catheter.

The selection of the best path is not a trivial operation. The sinuses are 3D spaces, and, especially if there is any sort of blockage between a nostril and the selected region, the best path may comprise a relatively complicated route. In addition, while the CT scan can be used to generate 3D images, the analysis of such images, because they are three-dimensional, is difficult and time-consuming.

U.S. Pat. No. 7,720,521 to Chang et al., whose disclosure is incorporated herein by reference, describes a system for performing image guided interventional and surgical procedures, including various procedures to treat sinusitis and other disorders of the paranasal sinuses.

U.S. Pat. No. 8,160,676 to Gielen et al., whose disclosure is incorporated herein by reference, describes a method for planning a surgical procedure. The plan can include a path or trajectory to reach a selected target.

U.S. Patent Application 2008/0183073, issued as U.S. Pat. No. 9,155,492 on Oct. 13, 2015, to Higgins et al., whose disclosure is incorporated herein by reference, describes methods to assist in planning routes through hollow, branching organs in patients to optimize subsequent endoscopic procedures.

U.S. Pat. No. 8,116,847 to Gattani et al., whose disclosure is incorporated herein by reference, describes a method for calculating an optimum surgical trajectory or path for displacing a surgical instrument through the interior of the body of a patient.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

receiving a computerized tomography (CT) scan of at least a part of a body of a patient;

identifying voxels of the scan that correspond to regions in the body that are traversable by a probe inserted therein;

displaying the scan on a screen and marking thereon selected start and termination points for the probe;

finding a path from the start point to the termination point comprising a connected set of the identified voxels;

using the scan to generate a representation of an external surface of the body and displaying the representation on the screen; and rendering an area of the external surface surrounding the path locally transparent in the displayed representation, so as to make visible on the screen an internal structure of the body in a vicinity of the path.

Typically, identifying the voxels of the scan includes selecting mucous as a traversable species. Alternatively or additionally, identifying the voxels of the scan includes identifying soft tissue as a traversable species. Further alternatively or additionally identifying the voxels of the scan includes defining a range of Hounsfield units for voxels.

In a disclosed embodiment finding the path includes ensuring that no portion of the path includes a radius of curvature smaller than a range of possible radii of curvature of the probe.

In a further disclosed embodiment finding the path includes ensuring that a path diameter is always larger than a diameter of the probe.

In a yet further disclosed embodiment, finding the path includes finding a shortest path from the start point to the termination point. Typically, finding the shortest path includes using Dijkstra's algorithm or an extension thereof.

In an alternative embodiment finding the path includes ensuring that the probe is not required to traverse a portion of the path having a path radius curvature smaller than a probe radius of curvature achievable at the portion.

In a further alternative embodiment receiving the CT scan includes receiving one of an X-ray CT scan and a magnetic resonance imaging CT scan.

There is further provided, according to an embodiment of the present invention, apparatus, including:

a screen configured to display a computerized tomography (CT) scan of at least a part of a body of a patient; and a processor configured to:

receive the scan, identify voxels of the scan that correspond to regions in the body that are traversable by a probe inserted therein, mark on the screen selected start and termination points for the probe, find a path from the start point to the termination point comprising a connected set of the identified voxels, use the scan to generate a representation of an external surface of the body and display the representation on the screen, and render an area of the external surface surrounding the path locally transparent in the displayed representation, so as to make visible on the screen an internal structure of the body in a vicinity of the path.

The present disclosure will be more fully understood from the following detailed description of the embodiments thereof, taken together with the drawings, in which:

DETAILED DESCRIPTION OF EMBODIMENTS

Overview

Embodiments of the present invention assist a physician, by automatically selecting in a surgery pre-planning procedure the best path to be taken by a catheter, and by displaying the selected path on an image of the patient. The patient image is based on the region of the patient where the procedure is to be performed.

A computerized tomography (CT) scan, typically an X-ray CT scan, of the procedure region is received, and voxels of the scan corresponding to regions of the body of the patient that are traversable by a probe to be inserted into the patient are identified. The identification is typically by defining a range of Hounsfield units for the voxels.

The physician displays the scan on a screen, and marks on the scan start and termination points for the probe.

A processor uses an algorithm, such as Dijksbra's algorithm, to find a path, typically the shortest path, from the start point to the termination point that has a connected set of the identified voxels.

The processor also generates a representation of an external surface of the body and the representation is displayed on the screen. The processor then renders an area of the external surface surrounding the path locally transparent in the displayed representation, so as to make visible on the screen an internal structure of the body in a vicinity of the path.

DETAILED DESCRIPTION

Figure 1:
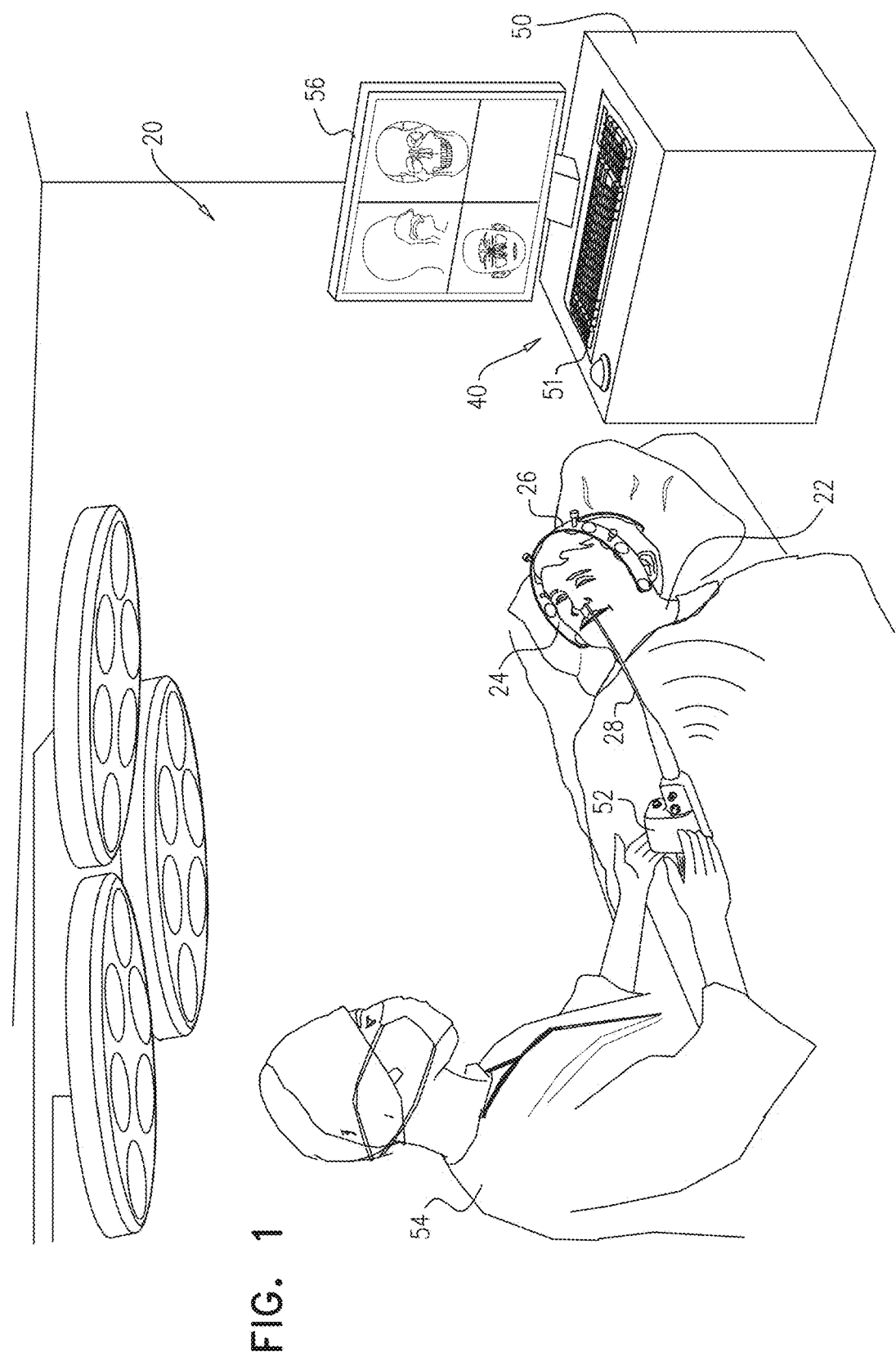
FIG. 1 is a schematic illustration of a nasal sinus surgery system, according to an embodiment of the present invention.

Reference is now made to FIG. 1, which is a schematic illustration of a nasal sinus surgery system 20, according to an embodiment of the present invention. System 20 is typically used during an invasive procedure on a nasal sinus of a patient 22, and the system includes a surgery pre-planning component, described in more detail below.

For the actual procedure, a set of magnetic field generators 24 may be fixed to the head of the patient, for example by incorporating the generators into a frame which is clamped to the patient's head. The field generators enable the position of a probe 28 that is inserted into the nasal sinus of the patient to be tracked. A system using magnetic field generators, such as generators 24, for tracking an entity inserted into a patient is described in U.S. patent application Ser. No. 14/792,823, published as U.S. Pub. No. 2016/0007842 on Jan. 14, 2016, to Govari et al., which is incorporated herein by reference. In addition, the Carto® system produced by Biosense Webster, of Diamond Bar, Calif., uses a tracking system similar to that described herein for finding the location and orientation of a coil in a region irradiated by magnetic fields.

Elements of system 20, including generators 24, may be controlled by a system processor 40, comprising a processing unit communicating with one or more memories. Processor 40 may be mounted in a console 50, which comprises operating controls 51 that typically include a keypad and/or a pointing device such as a mouse or trackball. Console 50 also connects to other elements of system 20, such as a proximal end 52 of probe 28. A physician 54 uses the operating controls to interact with the processor while performing the procedure, and the processor may present results produced by system 20 on a screen 56.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Figure 2:
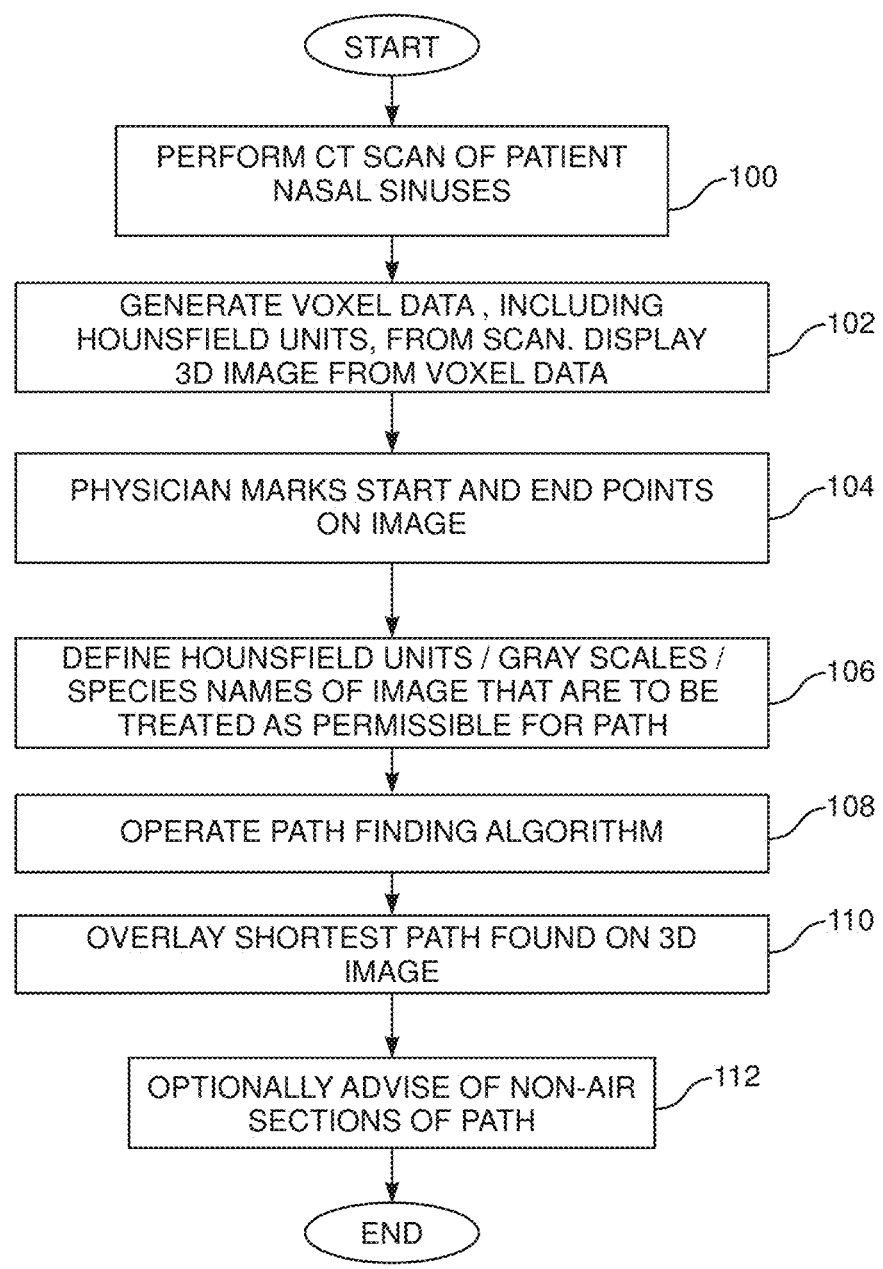
FIG. 2 is a flowchart showing steps of a surgery preplanning component of the system, according to an embodiment of the present invention.

FIG. 2 is a flowchart showing steps of the surgery pre-planning component referred to above, and FIGS. 3-8 are diagrams illustrating the steps, according to an embodiment of the present invention. The pre-planning component described by the flowchart is typically implemented prior to performance of the invasive surgery procedure on patient 22, and determines an optimal path to be followed by invasive probe 28 in the procedure. The pre-planning is assumed to be performed by physician 54.

In an initial step 100 of the flowchart, a computerized tomography (CT) X-ray scan of the nasal sinuses of patient 22 is performed, and the data from the scan is acquired by processor 40. As is known in the art, the scan comprises two-dimensional X-ray "slices" of the patient, and the combination of the slices generates three-dimensional voxels, each voxel having a Hounsfield unit, a measure of radiodensity, determined by the CT scan.

In an image generation step 102, physician 54 displays results of the scan on screen 56. As is known in the art, the results may be displayed as a series of two-dimensional (2D) slices, typically along planes parallel to the sagittal, coronal, and/or transverse planes of patient 22, although other planes are possible. The direction of the planes may be selected by the physician.

Figure 3:
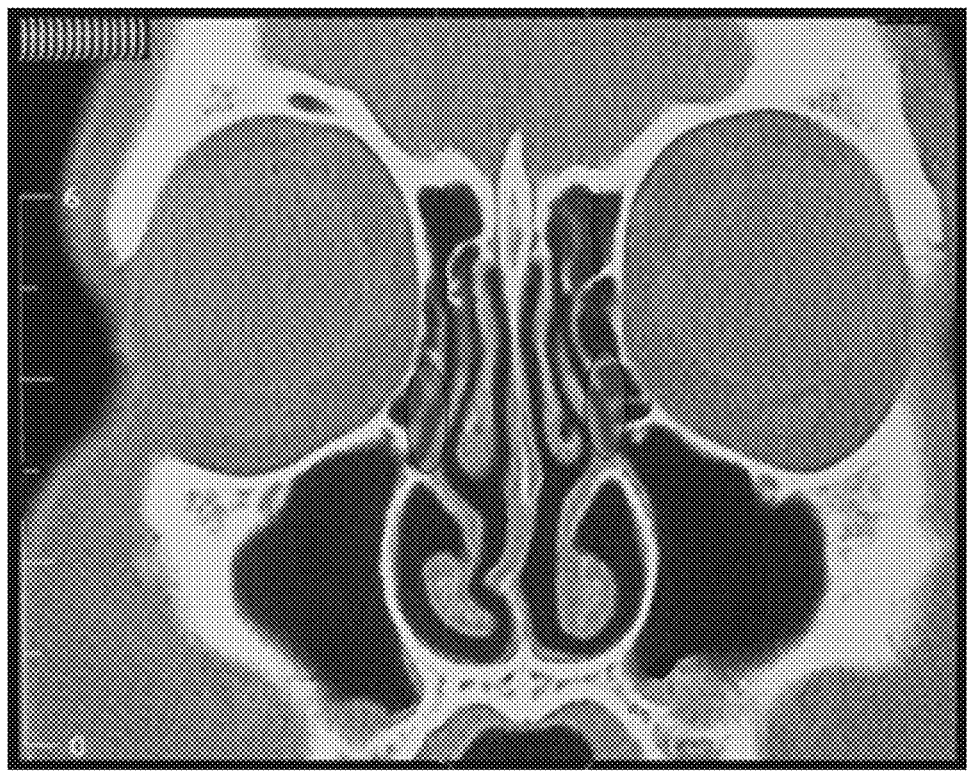
FIGS. 3-8 are diagrams illustrating the steps of the flowchart, according to an embodiment of the present invention.

The displayed results are typically gray scale images, and an example is provided in FIG. 3, which is a slice parallel to the coronal plane of patient 22. The values of the gray scales, from black to white, may be correlated with the Hounsfield unit (HU) of the corresponding voxels, so that, as applies to the image of FIG. 3, air having HU=−1000 may be assigned to be black, and dense bone having HU=3000 may be assigned to be white.

As is known in the art, apart from the values for air and water, which by definition are respectively −1000 and 0, the value of the Hounsfield unit of any other substance or species, such as dense bone, is dependent, inter alia, on the spectrum of the irradiating X-rays used to produce the CT scans referred to herein. In turn, the spectrum of the X-rays depends on a number of factors, including the potential in kV applied to the X-ray generator, as well as the composition of the anode of the generator. For clarity in the present disclosure, the values of Hounsfield units for a particular substance or species are assumed to be as given in Table I below.

TABLE I

| Species/Substance | Hounsfield Unit |
| --- | --- |
| Air | −1000 |
| Soft Tissue | −300 to −100 |
| Fat | −50 |
| Water | 0 |
| Blood | +30 to +45 |
| Dense Bone | +3000 |

However the numerical values of HUs for particular species (other than air and water) as given in Table I are to be understood as being purely illustrative, and those having ordinary skill in the art will be able to modify these illustrative values, without undue experimentation, according to the species and the X-ray machine used to generate the CT images referred to herein.

Typically, a translation between HU values and gray scale values is encoded into a DICOM (Digital Imaging and Communications in Medicine) file that is the CT scan output from a given CT machine. For clarity in the following description the correlation of HU=−1000 to black, and HU=3000 to white, and correlations of intermediate HU values to corresponding intermediate gray levels is used, but it will be understood that this correlation is purely arbitrary. For example, the correlation may be "reversed," i.e., HU=−1000 may be assigned to white, HU=3000 assigned to black, and intermediate HU values assigned to corresponding intermediate gray levels. Thus, those having ordinary skill in the art will be able to adapt the description herein to accommodate other correlations between Hounsfield units and gray levels, and all such correlations are assumed to be comprised within the scope of the present invention.

Figure 4:
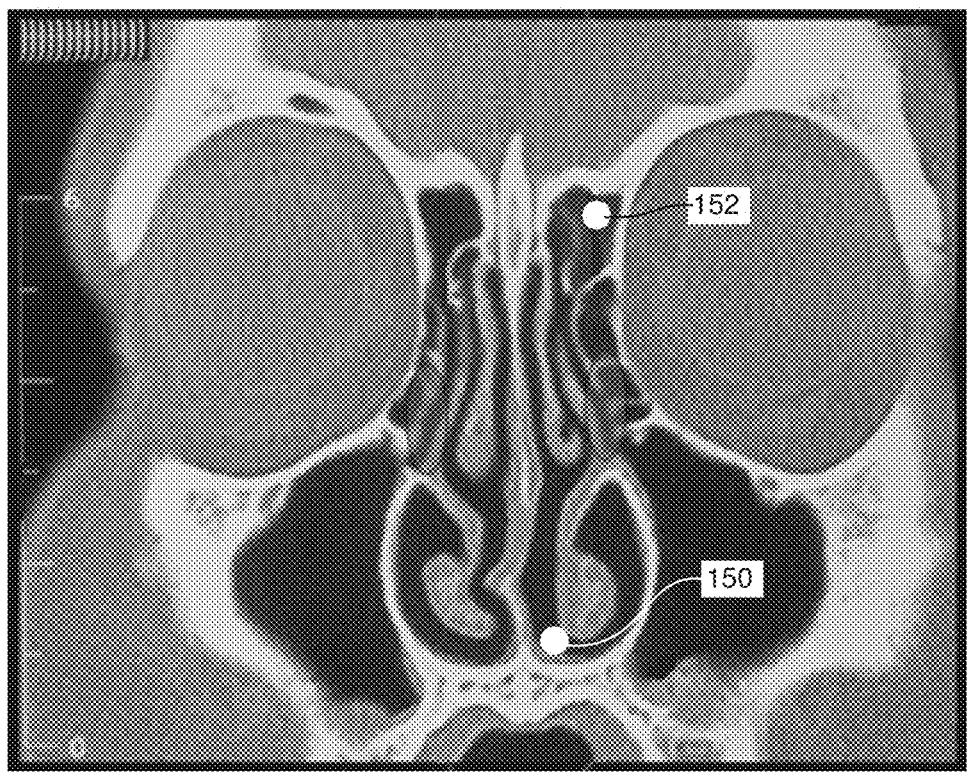

In a marking step 104 the physician marks an intended start point, where he/she will insert probe 28 into the patient, and an intended target point, where the distal end of the probe is to terminate. The two points may be on the same 2D slice. Alternatively, each point may be on a different slice. Typically, both points are in air, i.e., where HU=−1000, and the termination point is usually, but not necessarily, at a junction of air with liquid or tissue shown in the slice. (An example where the termination point is not at such a junction is when the point may be in the middle of an air-filled chamber.) FIG. 4 illustrates a start point 150 and a termination point 152 that are marked on the same 2D slice by the physician, and for clarity these points are assumed, except where otherwise stated, to be the points used in the remaining description of the flowchart. Typically the start and termination points are displayed in a non-gray scale color, for example, red.

In a permissible path definition step 106, the physician defines ranges of Hounsfield units which the path finding algorithm, referred to below, uses as acceptable voxel values in finding a path from start point 150 to termination point 152. The defined range typically includes HUs equal to −1000, corresponding to air or a void in the path; the defined range may also include HUs greater than −1000, for example, the range may be defined as given by expression (1):

$$\{HU|-1000 \leq HU \leq U\} \quad (1)$$

where U is a value selected by the physician.

For example U may be set to +45, so that the path taken may include water, fat, blood, soft tissue as well as air or a void.

There is no requirement that the defined range of values is a continuous range, and the range may be disjoint, including one or more sub-ranges. In some embodiments a sub-range may be chosen to include a specific type of material. An example of a disjoint range is given by expression (2):

$$\{HU|HU=-1000 \text{ or } A \leq HU \leq B\} \quad (2)$$

where A, B are values selected by the physician.

For example A, B may be set to be equal to −300 and −100 respectively, so that the path taken may include air or a void and soft tissue.

The method of selection for the range of HUs for the may be by any convenient method known in the art, including, but not being limited to, by number, and/or by name of material, and/or by gray scale. For example, in the case of selection by gray scale, physician 54 may select one or more regions of the CT image, and the HU equivalents of the gray scale values of the selected regions are included in the acceptable range of HUs for voxels of the path to be determined by the path finding algorithm.

In the case of selection by name, a table of named species may be displayed to the physician. The displayed table is typically similar to Table I, but without the column giving values of Hounsfield units. The physician may select one or more named species from the table, in which case the HU equivalents of the selected named species are included in the acceptable range of HUs for voxels of the path to be determined by the path finding algorithm.

In a path finding step 108, processor 40 implements a path finding algorithm to find one or more shortest paths, between start point 150 and termination point 152, that is to be followed by probe 28. The algorithm assumes that traversable voxels in the path include any voxels having HUs in the HU range defined in step 106, and that voxels having HU values outside this defined range act as barriers in any path found. While the path finding algorithm used may be any algorithm that is able to determine a shortest path within a three-dimensional maze, the inventors have found that the Flood Fill algorithm, Dijkstra's algorithm, or an extension such as the A* algorithm, give better results in terms of speed of computation and accuracy of determining the shortest path than other algorithms such as Floyd's algorithm or variations thereof.

In some embodiments, the path finding step includes taking account of mechanical properties and dimensions of probe 28. For example, in a disclosed embodiment, probe 28 may be limited, when it bends, to a range of possible radii of curvature. In determining possible paths to be followed by the probe, the processor ensures that no portion of the path defines a radius less than this range of radii.

In a further disclosed embodiment, the processor takes account of probe mechanical properties that permit different portions of the probe different ranges of radii of curvature. For example, the end of a possible path may have a smaller radius of curvature than the possible radii of curvature of a proximal part of the probe. However, the distal end of the probe may be more flexible than the proximal part, and may be flexible enough to accommodate the smaller radius of curvature, so that the possible path is acceptable.

In considering the possible radii of curvature of the probe, and the different radii of curvature of possible paths, the processor takes into account which portions of a path need to be traversed by different portions of the probe, and the radii of curvature achievable by the probe, as the distal end of the probe moves from start point 150 to termination point 152.

In a yet further disclosed embodiment, the processor ensures that a path diameter D is always larger than a measured diameter d of probe 28. The confirmation may be at least partially implemented, for example, by the processor using erosion/dilation algorithms, as are known in the art, to find voxels within the ranges defined in step 106.

Figure 5:
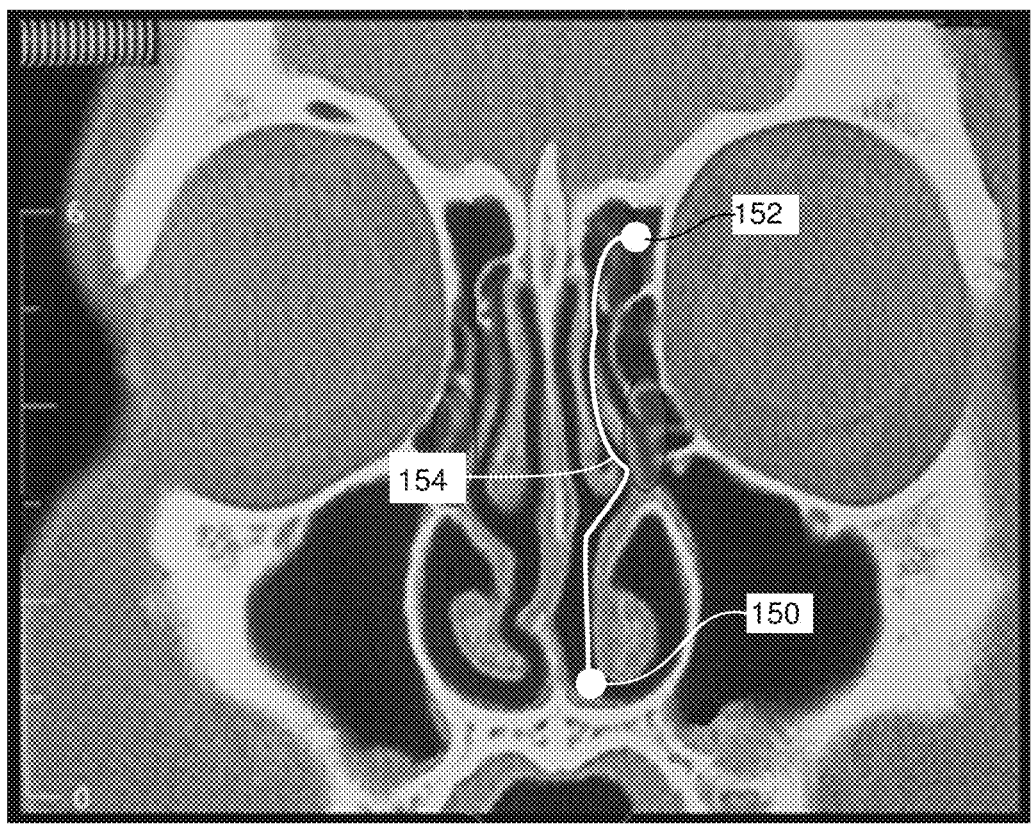

In an overlay step 110, the shortest path found in step 108 is overlaid on an image that is displayed on screen 56. FIG. 5 illustrates a shortest path 154, between start point 150 and termination point 152, that has been overlaid on the image of FIG. 4. Typically path 154 is displayed in a non-gray scale color, which may or may not be the same color as the start and termination points. In the case that step 108 finds more than one shortest path, all such paths may be overlaid on the image, typically in different non-gray scale colors.

Typically the path found traverses more than one 2D slice, in which case the overlaying may be implemented by incorporating the path found into all the 2D slices that are relevant, i.e., through which the path traverses. Alternatively or additionally, an at least partially transparent 3D image may be generated from the 2D slices of the scan, and the path found may be overlaid on the 3D image. The at least partially transparent 3D image may be formed on a representation of an external surface of patient 22, as is described in more detail below.

Figure 6:
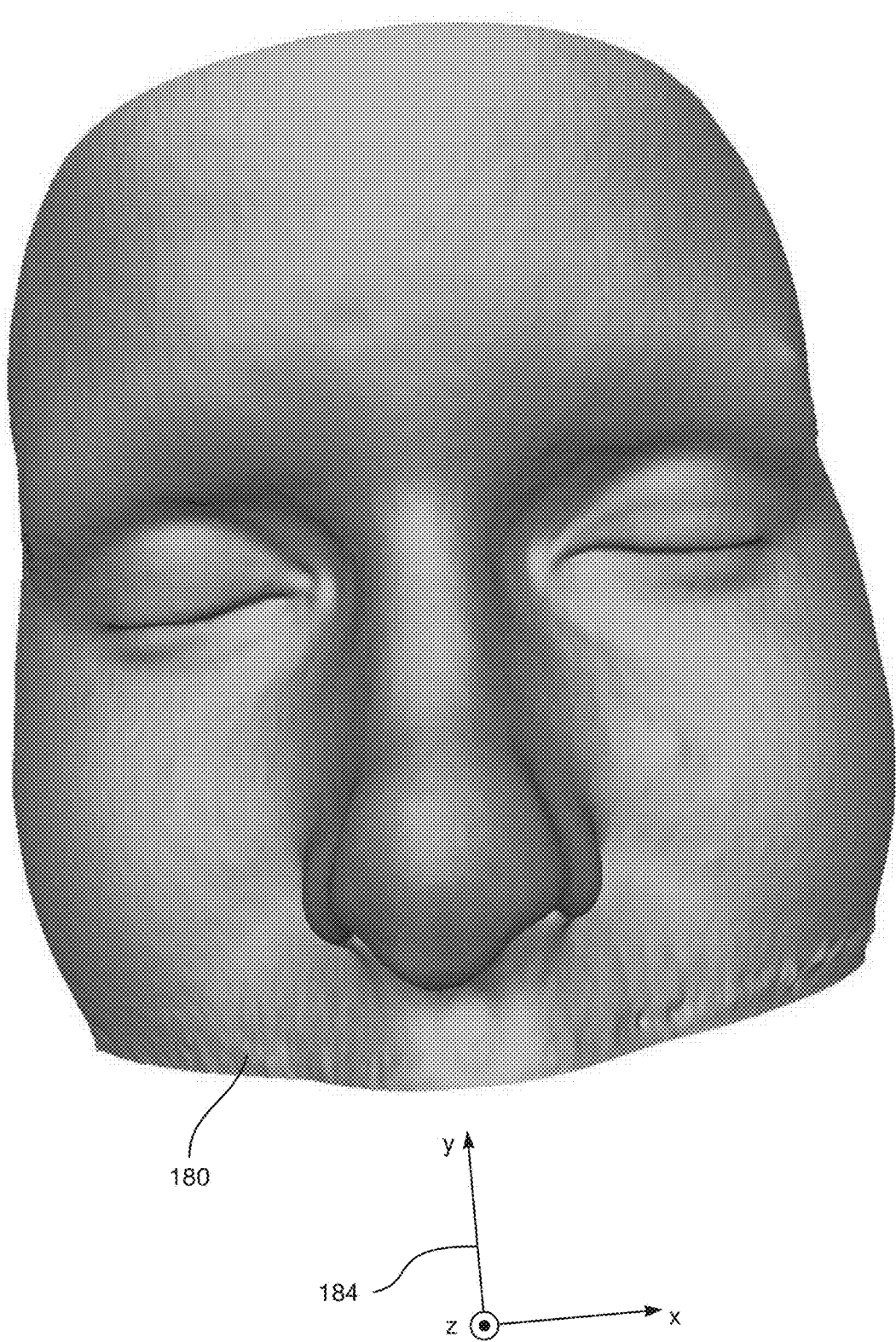

FIG. 6 is a representation of an external surface 180 of patient 22, according to an embodiment of the present invention. Processor 40 uses the CT scan data acquired in step 100 to generate the representation of the external surface, by using the facts that air has an HU value of −1000 while skin has an HU value significantly different from this. By way of example, representation 180 is assumed to be formed on a plane parallel to the coronal plane of the patient, i.e., parallel to an xy plane of a frame of reference 184 defined by the patient, the axes of which are also drawn in FIG. 6 and in FIG. 7 below.

Figure 7:
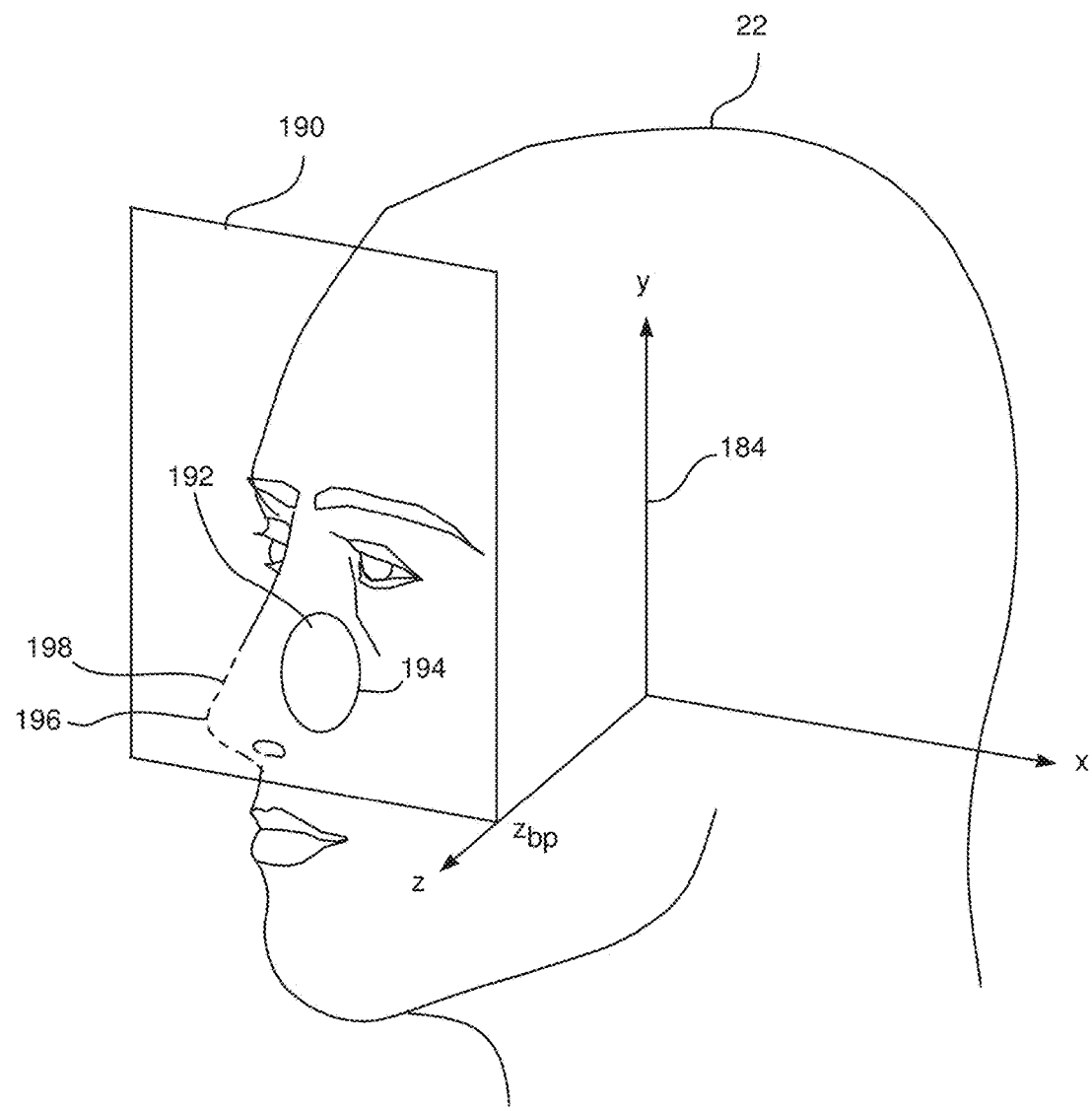

FIG. 7 schematically illustrates a boundary plane 190 and a bounding region 192, according to an embodiment of the present invention. Under directions from physician 54, processor 40 delineates regions of representation 180 which are to be rendered transparent, and those which are to be left "as is." In order to perform the delineation, the physician defines boundary plane 190, and bounding region 192 in the boundary plane, using a bounding perimeter 194 for the region.

For clarity, the following description assumes that the boundary plane is parallel to an xy plane of frame of reference 184, as is illustrated schematically in FIG. 7, and that it has an equation given by:

$$z = z_{bp} \quad (3)$$

As described below, processor 40 uses the boundary plane and the bounding region to determine which elements of surface 180 are to be rendered locally transparent, and which elements are not to be so rendered.

Processor 40 determines elements of surface 180 (FIG. 6) having values of $z \geq z_{bp}$, and that, when projected along the z-axis, lie within area 192. The processor then renders the elements transparent so that, consequently, these elements are no longer visible in surface 180. For example, in FIG. 7 a tip 196 of the nose of patient 22 has a value $z \geq z_{bp}$, so a broken line 198 in the vicinity of the patient's nose tip illustrates parts of external surface 180 that are no longer visible when the image of the surface is presented on screen 56.

In consequence of the above-defined elements being rendered transparent, elements of surface 180, having values of $z \leq z_{bp}$ and that when projected along the z-axis lie within area 192 are now visible, so are displayed in the image. Prior to the local transparent rendering, the "now visible" elements were not visible since they were obscured by surface elements. The now visible elements include elements of shortest path 154, as is illustrated in FIG. 8.

Figure 8:
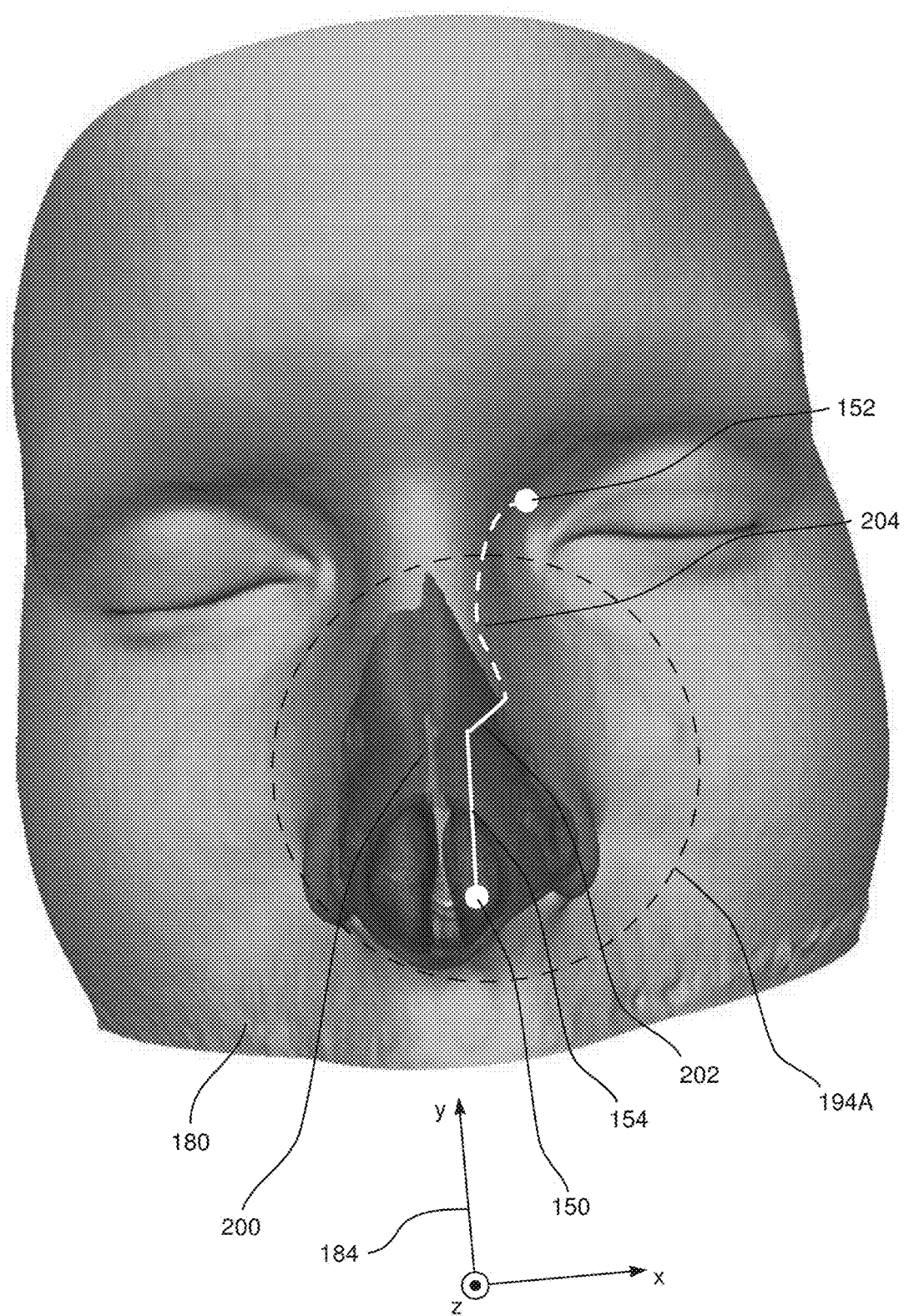

FIG. 8 schematically illustrates surface 180 as displayed on screen 56 after the local transparency rendering of the elements of the surface within area 170. For clarity a broken circle 194A, corresponding to perimeter 194 (FIG. 6) has been overlaid on the image, and frame of reference 184 is also drawn in the figure. Because of the transparent rendering of elements within circle 194A, an area 200 within the circle now shows internal structure, derived from the CT tomographic data received in step 100, of subject 22.

Shortest path 154 has also been drawn in FIG. 8. Because of the transparent rendering of elements within circle 194A, a portion of the path is now visible in the image of surface 180, and has been drawn as a solid while line 202. The portion of the path that is invisible, because it is hidden by elements of surface 180 that have not been rendered transparent, is shown as broken white line 204.

It will be appreciated that in the case illustrated in FIGS. 6 and 8 screen 56 is in an xy plane, so that the screen acts as a "virtual camera" of a viewer looking towards surface 180 along a z axis.

The description above provides one example of the application of local transparency to viewing a shortest path derived from tomographic data, the local transparency in this case being formed relative to a plane parallel to the coronal plane of the subject. It will be understood that because of the three-dimensional nature of the tomographic data, the data may be manipulated so that embodiments of the present invention may view the shortest path using local transparency formed relative to substantially any plane through patient 22, and that may be defined in frame of reference 184.

In forming the local transparency, the dimensions and position of the bounding plane and the bounding region may be varied to enable the physician to also view the shortest path, and internal structures in the vicinity of the path.

The physician may vary the direction of the bounding plane, for example to enhance the visibility of particular internal structures. While the bounding plane is typically parallel to the plane of the image presented on screen 56, this is not a requirement, so that if, for example, the physician wants to see more detail of a particular structure, she/he may rotate the bounding plane so that it is no longer parallel to the image plane.

In some cases the range of HU values/gray scales selected in step 106 includes regions other than air, for example, regions that correspond to soft tissue and/or mucous. The path found in step 108 may include such regions, and in this case, for probe 28 to follow the path, these regions may have to be cleared, for example by debriding. In an optional warning step 112, the physician is advised of the existence of regions of path 154 that are not in air, for example by highlighting a relevant section of the path, and/or by other visual or auditory cues.

While the description above has assumed that the CT scan is an X-ray scan, it will be understood that embodiments of the present invention comprise finding a shortest path using MRI (magnetic resonance imaging) tomography images.

Thus, referring back to the flowchart, in the case of MRI images, wherein Hounsfield values may not be directly applicable, in step 106 the physician defines ranges of gray scale values (of the MRI images) which the path finding algorithm uses as acceptable voxel values in finding a path from the start point to the termination point. In step 108, the path finding algorithm assumes that traversable voxels in the path include any voxels having gray scales in the gray scale range defined in step 106, and that voxels having gray scale values outside this defined range act as barriers in any path found. Other changes to the description above, to accommodate using MRI images rather than X-ray CT images, will be apparent to those having ordinary skill in the art, and all such changes are to be considered as comprised within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
(a) receiving a computerized tomography (CT) scan of at least a part of a body of a patient;
(b) identifying voxels of the scan that correspond to regions in the body;
(c) displaying the scan on a screen and marking thereon selected start and termination points for a probe inserted in the body;
(d) finding a path from the start point to the termination point comprising a connected set of the identified voxels that are traversable by the probe, wherein finding the path comprises determining a set of density data associated with each of the identified voxels, determining a traversable density range, and determining the connected set of the identified voxels based at least upon the set of density data associated with those voxels being within the traversable density range;
(e) using the scan to generate a representation of an external surface of the body and displaying the representation on the screen;
(f) selecting a first region of the representation of the external surface to be transparent, wherein the first region is associated with the path such that the path is viewable through the first region;
(g) selecting a second region of the representation of the external surface to be non-transparent;
(h) rendering the first region transparent in the displayed representation, so as to make visible on the screen an internal structure of the body in a vicinity of the path; and
(i) rendering the second region non-transparent while rendering the first region transparent;
wherein the traversable density range comprises at least one density other than the density of air.

2. The method according to claim 1, wherein finding the path comprises ensuring that no portion of the path comprises a radius of curvature smaller than a range of possible radii of curvature of the probe.

3. The method according to claim 1, wherein finding the path comprises ensuring that a path diameter is always larger than a diameter of the probe.

4. The method according to claim 1, wherein finding the path comprises finding a shortest path from the start point to the termination point, and wherein the path is configured to be viewable through the first region as a line with a first visual style, and wherein the path is configured to be viewable through the second region as a line with a second visual style.

5. The method according to claim 1, wherein finding the path comprises:
(i) identifying a distal portion of the path having a first radius of curvature and a proximal portion of the path having a second radius of curvature,
(ii) determining whether a distal part of the probe is capable of the first radius of curvature, and
(iii) determining whether a proximal part of the probe is capable of the second radius of curvature,
wherein the distal portion of the path and the proximal portion of the path are positioned such that the distal part of the probe would arrive at the distal portion of the path at the same moment that the proximal part of the probe arrives at the proximal portion of the path.

6. The method according to claim 1, wherein receiving the CT scan comprises receiving one of an X-ray CT scan and a magnetic resonance imaging CT scan, further comprising:
(a) identifying one or more regions of the path that pass through a material other than air based upon the set of density data, and
(b) visually marking the one or more regions of the path to indicate that they pass through a material other than air.

7. The method of claim 1, wherein determining the traversable density range comprises presenting a density selection interface to a user and receiving the traversable density range as a user input via the density selection interface.

8. The method of claim 7, wherein the density selection interface comprises an image of the scan, and wherein receiving the traversable density range comprises receiving input from the user selecting one or more traversable regions of the image, determining traversable densities associated with the one or more traversable regions based upon the set of density data, and associating those traversable densities with the traversable density range.

9. The method of claim 7, wherein receiving the traversable density range comprises receiving one or more Hounsfield units, receiving one or more comparison operators, and generating a range expression for the traversable density range based upon the one or more Hounsfield units and the one or more comparison operators.

10. The method of claim 7, wherein the density selection interface comprises a set of materials, each of the set of materials associated with a density, and wherein receiving the traversable density range comprises receiving input from the user selecting one or more of the set of materials and associating the density of each of the selected one or more of the set of materials with the traversable density range.

11. Apparatus, comprising:
(a) a screen configured to display a computerized tomography (CT) scan of at least a part of a body of a patient; and
(b) a processor configured to perform the following:
(i) receive the scan,
(ii) identify voxels of the scan that correspond to regions in the body,
(iii) mark on the screen selected start and termination points for a probe inserted in the body,
(iv) find a path from the start point to the termination point comprising a connected set of the identified voxels that are traversable by the probe, wherein the processor is configured to find the path by determining a set of density data associated with each of the identified voxels, determining a traversable density range, and determining the connected set of the identified voxels based at least upon the set of density data associated with those voxels being within the traversable density range,
(v) use the scan to generate a representation of an external surface of the body and display the representation on the screen,
(vi) select a first region of the representation of the external surface to be transparent, wherein the first region is associated with the path such that the path is viewable through the first region,
(vii) select a second region of the representation of the external surface to be non-transparent, (viii) render the first region transparent in the displayed representation, so as to make visible on the screen an internal structure of the body in a vicinity of the path, and (ix) render the second region non-transparent while rendering the first region transparent;

wherein the traversable density range comprises at least one density other than the density of air.

12. The apparatus according to claim 11, wherein finding the path comprises ensuring that no portion of the path comprises a radius of curvature smaller than a range of possible radii of curvature of the probe.

13. The apparatus according to claim 11, wherein finding the path comprises ensuring that a path diameter is always larger than a diameter of the probe.

14. The apparatus according to claim 11, wherein finding the path comprises finding a shortest path from the start point to the termination point, and wherein the path is configured to be viewable through the first region as a line with a first visual style, and wherein the path is configured to be viewable through the second region as a line with a second visual style.

15. The apparatus according to claim 11, wherein the processor is configured to find the path by:
(i) identifying a distal portion of the path having a first radius of curvature and a proximal portion of the path having a second radius of curvature,
(ii) determining whether a distal part of the probe is capable of the first radius of curvature, and
(iii) determining whether a proximal part of the probe is capable of the second radius of curvature,
wherein the distal portion of the path and the proximal portion of the path are positioned such that the distal part of the probe would arrive at the distal portion of the path at the same moment that the proximal part of the probe arrives at the proximal portion of the path.

16. The apparatus according to claim 11, wherein receiving the CT scan comprises receiving one of an X-ray CT scan, a magnetic resonance imaging CT scan, and where the processor is further configured to:
(i) identify one or more regions of the path that pass through a material other than air based upon the set of density data, and
(ii) visually mark the one or more regions of the path to indicate that they pass through a material other than air.

17. The apparatus of claim 11, wherein determining the traversable density range comprises presenting a density selection interface to a user and receiving the traversable density range as a user input via the density selection interface.

18. The apparatus of claim 17, wherein the density selection interface comprises an image of the scan, and wherein receiving the traversable density range comprises receiving input from the user selecting one or more traversable regions of the image, determining traversable densities associated with the one or more traversable regions based upon the set of density data, and associating those traversable densities with the traversable density range.

19. The apparatus of claim 17, wherein receiving the traversable density range comprises receiving one or more Hounsfield units, receiving one or more comparison operators, and generating a range expression for the traversable density range based upon the one or more Hounsfield units and the one or more comparison operators.

20. The apparatus of claim 17, wherein the density selection interface comprises a set of materials, each of the set of materials associated with a density, and wherein receiving the traversable density range comprises receiving input from the user selecting one or more of the set of materials and associating the density of each of the selected one or more of the set of materials with the traversable density range.

* * * * *